US010091143B2

(12) United States Patent
Blahnik et al.

(10) Patent No.: US 10,091,143 B2
(45) Date of Patent: Oct. 2, 2018

(54) DYNAMIC RULE-BASED NOTIFICATIONS

(71) Applicant: Apple Inc., Cupertino, CA (US)

(72) Inventors: Jay Kriz Blahnik, San Francisco, CA (US); Eric D. Schlakman, San Francisco, CA (US); Siji Rachel Tom, Sunnyvale, CA (US); Daniel S. Keen, San Jose, CA (US); Aaron P. Thompson, San Francisco, CA (US); Jed R. Cohen, Santa Clara, CA (US); Tasha R. Klubock, Oakland, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/798,234

(22) Filed: Oct. 30, 2017

(65) Prior Publication Data

US 2018/0048598 A1 Feb. 15, 2018

Related U.S. Application Data

(63) Continuation of application No. 14/740,004, filed on Jun. 15, 2015, now Pat. No. 9,819,617.
(Continued)

(51) Int. Cl.
*G06F 15/16* (2006.01)
*H04L 12/58* (2006.01)
(Continued)

(52) U.S. Cl.
CPC .......... *H04L 51/043* (2013.01); *A61B 5/1118* (2013.01); *A61B 5/681* (2013.01);
(Continued)

(58) Field of Classification Search
None
See application file for complete search history.

(56) References Cited

U.S. PATENT DOCUMENTS 7,130,664 B1    10/2006  Williams
7,662,065 B1     2/2010  Kahn et al.
(Continued)

FOREIGN PATENT DOCUMENTS

CN    103592837 A     2/2014
CN    104076682 A    10/2014
(Continued)

OTHER PUBLICATIONS

International Application PCT/US2016/012280, International Search Report and Written Opinion dated Apr. 6, 2016, 9 pages.
(Continued)

*Primary Examiner* — Joshua Joo
(74) *Attorney, Agent, or Firm* — Kilpatrick Townsend & Stockton LLP

(57) ABSTRACT

Systems, methods, and computer-readable medium are provided for providing dynamic rule-based messages. For example, a user device may identify physical activity information. Based at least in part on the activity information, the device may determine whether a physical activity goal has been reached. The device may determine whether to present a dynamic progress update message based at least in part on a time since a first activity message was presented and whether the physical activity goal has been reached. In some instances, when it is determined to present the dynamic progress update message, the device may access a data structure configured to maintain progress update information associated with respective time intervals. The device may then retrieve the dynamic progress update message that corresponds to a particular time interval from the data structure. The device may also present the message for the particular time interval.

20 Claims, 10 Drawing Sheets

Related U.S. Application Data

(60) Provisional application No. 62/127,626, filed on Mar. 3, 2015.

(51) Int. Cl.
    *A61B 5/11*    (2006.01)
    *A61B 5/00*    (2006.01)
    *G06F 19/00*    (2018.01)
    *A61B 5/0205*    (2006.01)

(52) U.S. Cl.
    CPC ........ *G06F 19/3481* (2013.01); *H04L 51/046* (2013.01); *A61B 5/0205* (2013.01)

(56) References Cited

U.S. PATENT DOCUMENTS

| | | |
|---|---|---|
| 8,610,582 B2 | 12/2013 | Jeon et al. |
| 8,954,290 B2* | 2/2015 | Yuen ............... H04W 4/21 702/160 |
| 9,329,053 B2 | 5/2016 | Lakovic et al. |
| 2011/0035292 A1 | 2/2011 | Boesel et al. |
| 2012/0253485 A1 | 10/2012 | Weast et al. |
| 2013/0106684 A1 | 5/2013 | Weast et al. |
| 2014/0240122 A1 | 8/2014 | Roberts et al. |
| 2014/0273978 A1 | 9/2014 | Van Snellenberg |
| 2015/0205465 A1* | 7/2015 | Robison ............... G06F 3/0484 715/744 |
| 2016/0077495 A1 | 3/2016 | Brown et al. |
| 2016/0096074 A1 | 4/2016 | Moll-Carrillo et al. |
| 2016/0166156 A1 | 6/2016 | Yuen et al. |
| 2016/0166195 A1 | 6/2016 | Radecka et al. |

FOREIGN PATENT DOCUMENTS

| | | |
|---|---|---|
| EP | 2040211 | 3/2009 |
| WO | 2016140732 | 9/2016 |

OTHER PUBLICATIONS

Non-Final Office Action dated Feb. 28, 2017 in U.S. Appl. No. 14/740,004. 17 pages.

Notice of Allowance dated Jul. 14, 2017 in U.S. Appl. No. 14/740,004. 8 pages.

Chinese Office Action dated Jul. 13, 2018 in Application No. 201680012986.1. 22 pages (English translation of the pending claims, partial English translation of Action).

\* cited by examiner

_US 10,091,143 B2_

DYNAMIC RULE-BASED NOTIFICATIONS

CROSS-REFERENCES TO RELATED APPLICATIONS

The present application is a continuation of U.S. patent application Ser. No. 14/740,004 filed Jun. 15, 2015 which claims the benefit of and priority to U.S. Provisional Application No. 62/127,626, filed Mar. 3, 2015, the entire contents of which is incorporated herein by reference for all purposes.

BACKGROUND

Wearable devices and other peripheral user electronics are becoming more and more popular. Some of such devices may track the physical activity of a user using biometric sensors and/or motion detection devices. Additionally, these peripheral devices are typically smaller and more portable than traditional consumer electronics. Many of these activity tracking devices, however, are not typically worn by users except while exercising. But, as these devices become more user friendly and continue to add new functionality, more and more users may be wearing such devices throughout an entire day and relying on them for more than just activity tracking. Such devices may need to provide more relevant messages.

BRIEF SUMMARY

Embodiments of the present disclosure can provide systems, methods, and computer-readable medium for providing dynamic rule-based notifications (e.g., messages that are dynamically changed based on timing, progress, and/or the previous message). In some examples, a wearable device may track physical activity information of a user against one or more physical activity category goals.

According to one embodiment, a method may be executed by a wearable computer system to at least receive physical activity information. The wearable device may determine whether a physical activity goal has been reached with respect to a category of a plurality of activity categories. The determination may be based at least in part on the physical activity information. In some example, the wearable device may determine whether to present a new message based at least in part on a time since a previous message was presented on the wearable computing device and whether the physical activity goal has been reached. If the new message is to be presented, the wearable device may determine a highest scoring category of the plurality of activity categories, determine a time of day, select the dynamic progress update message from a plurality of dynamic progress update messages for the highest scoring category based at least in part on the time of day, and present the new message with the dynamic progress update message.

In some examples, the wearable device may estimate the physical activity goal based at least in part on a measured amount of physical activity for the category from a previous time period. The wearable device may also receive the goal via an input on the wearable computing device. In some cases, the wearable device may refrain from presenting any new messages with updates until after a period of time if the new message is not to be presented. The time of day may be determined based at least in part on an amount of time since the a first interaction with the wearable computing device and/or each of the plurality of dynamic progress update messages may be different for each different time of the day. In some examples, the dynamic progress update message may be different for each category of the plurality of activity categories (e.g., for the same time of the day) and/or the presentation timing between the new message and a next message including the dynamic progress update message may be different for each of the plurality of activity categories.

According to another embodiment, a computer-readable medium executed by a processor of a user device may include instructions that, when executed, configure a computer processor to identify physical activity information. The instructions may further configure the processor to determine, based at least in part on the physical activity information, whether a physical activity goal has been reached. The instructions may also configure the processor to determine whether to present the dynamic progress update message based at least in part on a time since a first activity message was presented and whether the physical activity goal has been reached. In some examples, when it is determined to present the dynamic progress update message, the instructions may configure the processor to access a data structure configured to maintain progress update information associated with respective time intervals. Further, the instructions may configure the processor to retrieve, from the data structure, the dynamic progress update message that corresponds to a particular time interval of the respective time intervals and/or present the dynamic progress update message for the particular time interval.

In some examples, the operations may further comprise determining the particular time interval for presenting the dynamic progress update message based at least in part on a time of a day or a segment of a calendar period. The physical activity information may be identified by a motion detection device coupled to the processor. Additionally, in some embodiments, the physical activity information may be identified by receiving the activity information via an input to a wearable device. In some cases, the activity goal may be selected via the input to the wearable device. The operations may further comprise presenting the first activity message when the activity goal is reached. And, the dynamic progress update may exclude the first activity message Further, in some examples, the data structure may include different progress update information for each of the respective time intervals, and the provided dynamic progress update may correspond to respective progress update information for the particular time interval.

According to another embodiment, a system may be implemented as a wearable computing device configured with a memory. The processor of the wearable computing device may be configured to execute instructions stored on the memory of the portable computing device to identify physical activity information collected by a wearable device. The processor of the wearable computing device may also be configured to identify a fitness goal. In some examples, the processor of the wearable device also may be configured to determine progress towards the fitness goal over a time period and/or prepare a user interface for presentation on the wearable device. In some examples, the determination may be based at least in part on the physical activity information and the fitness goal. Further, the user interface may be configured to present the dynamic progress update message based at least in part on the determined progress towards the fitness goal and a time interval of the time period associated with the identified physical activity information.

In some cases, the fitness goal may include an activity category of a plurality of activity categories, and the dynamic progress update message may be different for at least one activity category of the plurality of activity categories. Additionally, the dynamic progress update message may be presented based at least in part on a time since a previous progress update message. In some examples, the user interface may be further configured to present additional information in the dynamic progress update message, and the additional information may identify at least second progress towards a second fitness goal for the time interval of the time period.

DETAILED DESCRIPTION

Figure 1:
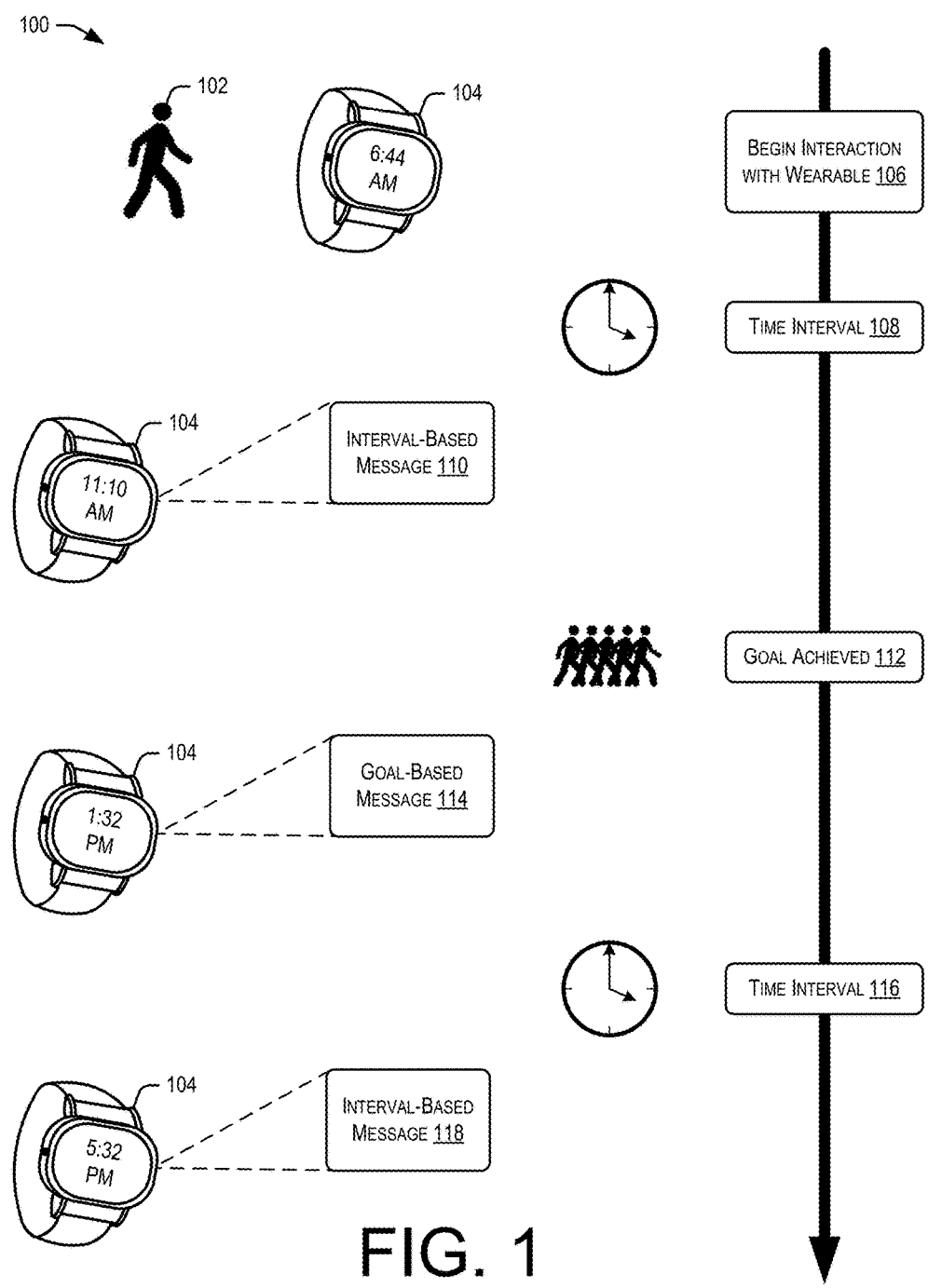
FIG. 1 is a simplified block diagram illustrating at least some example techniques for providing dynamic rule-based messages as described herein, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, providing dynamic notifications (messages) to a user of a wearable device based at least in part on one or more rules. Generally, the rules may dictate what messages are to be provided and when to provide the messages. For example, messages may be different at different times within a period (e.g., an hour, a day, a month, etc.) for a given set of facts. In particular, a user may interact with a peripheral (wearable) device that tracks or otherwise collects physical activity information of the user. In some examples, the physical activity information of the user may be utilized by the wearable device (or a server computer system configured to process data for the wearable device) to track the user's activity against one or more activity goals. For example, the user may be wearing a wearable device (e.g., a smart watch, smart glasses, a mobile headset, or the like) that includes one or more sensors configured to detect activity and/or biometric information of the user as the user moves. In some examples, the user may set one or more activity goals for respective activity categories, and the wearable device may track the user's progress towards those goals. Messages may inform the user of their progress at intervals, based on progress, and/or based on the rules.

More specifically, coaching and/or achievement notifications may be provided dynamically and may change over time (e.g., over the course of a day or some other time period). In some examples, the same amount of tracked activity may illicit different messages at different times (e.g., of the day) depending on the progress of the user towards their set goals. In some cases, the headline of a message may identify an activity or activity category for which the user is closest to their goal. Other information may be provided in the message with lesser importance or with less visual prominence. Particular rules for each time interval within a period of activity and/or for each category of activity may be used to determine when to provide a message and what to include in the message. Some of the rules may be selected by a user of the device, while some of the rules may be selected by a developer or administer of the system. For example, a user may set the rules to have updates (messages) every "x" number of hours (e.g., two hours, four hours, etc.). However, an administrative rule may not allow the next scheduled update if another message (e.g., a progress update) has come within the "x" number of hours. In this case, the next scheduled update may be pushed out "x" hours from the last progress update. Additionally, a user may have set the rules so that the system provides progress updates any time a goal is reached.

In some examples, the wearable device may present a user interface (UI) for displaying the messages. A set of rings or lines (e.g., line graphs or the like) may be presented that indicate different exercise categories and respective goals. For example, categories may include standing, walking, calories burned, running, swimming, or the like. Similarly, respective goals may include the number of times a user has stood per time interval (e.g., per hour, per day, etc.) or the number of time intervals in which the user stood for a specific amount of time (e.g., 1 minute per hour), the number of steps walked or the distance walked, the number of steps run or the distance run, the number of calories burned, the number of laps swum, or the like. As such, each ring or line of the UI may be empty (e.g., the shape may be rendered with an outline, but there may be no fill within the shape) or non-existent (e.g., the shape may not be presented yet) at first, and may be filled in or extended, respectively, as the user progresses towards the goal. The ring or line may be completely filled in, or fully extended (depending on the UI configuration), when the goal is met. In some examples, the UI (rings, lines, etc.) may be included in the message when the message is provided, it may be persistent on the screen with messages interrupting that persistence, or it may be presented when the device detects that the user is interacting with the screen (e.g., when the device detects that the user is looking at or attempting to look at the screen. Additionally, in some examples, different amounts of data may be presented depending on the type of interaction of the user. For example, if the user briefly glances at the device, only a small amount of information may be provided (e.g., the rings, bars, or text about a goal or achievement. If the user looks at the device for a longer period of time, more information may be provided (e.g., progress towards each category, percentages, metrics remaining to meet a goal, likelihood of completing a goal, etc.), and if the user touches the screen or otherwise interacts beyond looking at the screen, even more information may be presented.

In one example, the user may utilize a smart watch (e.g., an electronic wrist watch or the like with computer processing, network interfaces, and/or one or more software applications) for telling the time, interacting with a smartphone (e.g., a mobile phone with computer processing, network interfaces, and one or more software applications), and/or tracking physical activity. The smartphone and the smart watch may be connected via one or more network connections (e.g., Bluetooth, WiFi, or the like) and may be configured to communicate with one another. Additionally, the smart watch and/or the smartphone may be configured to communicate with one or more service providers (e.g., via one or more network-accessible servers). In some examples, as described above, the smart watch may be configured to present messages generated by the smart watch, or the messages may be originated at the smartphone or the service provider and then received by the smart watch. In one example, a dynamic messaging system of a smart watch may provide messages for presentation. The messages may be set to be presented based at least in part on intervals that begin when a user begins interacting (e.g., wearing) the smart watch. In some examples, the first interval may begin when the user begins wearing the smart watch or when the user begins physical activity (e.g., when the user gets out of bed in the morning). The dynamic messaging system may collect physical activity information of the user, and track that information with respect to user goals for one or more activity categories. If the user attains a goal before the next scheduled progress update, the system may message the user about the attained goal and then reset the interval timer. That way, the user is not provided with messages too often. Once the next time interval ends, the system may determine what information to present to the user for the next scheduled progress update. In some cases, the message (progress update) may include information about which goal the user is closest to attaining. Or, put another way, the message may identify the "best" goal of the user. The "best" goal may be calculated based at least in part on collected physical activity information and a time of the period being tracked (e.g., a single day in this example).

While examples are given where the wearable device described herein is a smart watch, any consumer electronic devices may be configured to operate the features described herein. For example, the wearable device may be a headset, a portable audio or video device, a smart button (e.g., of a shirt), a smart belt buckle, or the like. Further, while the appropriate messages to be provided are described as being determined by the wearable device, it should be understood that any computing system (including the smartphone or the service provider computers) may be used to determine which messages to provide and when to provide them. For example, a remote service provider, external server, local area network device, or the like may be configured to determine the appropriate messages to provide (e.g., using application programming interface (API) method calls or the like).

FIG. 1 illustrates an example workflow 100 that shows example implementations of the dynamic messages described herein, where a user 102 may interact with any wearable device (e.g., a smart watch) 104. As noted, the smart watch may be equipped with one or more sensors for detecting physical activity (standing, walking, running, etc.) of the user 102. At 106, the user 102 may begin interaction with the smart watch 104. For example, the user 102 may place the smart watch 104 on their wrist (or other body part), the user 102 may activate an application for tracking physical activity, or the user 102 may get up from lying down (signifying that the user has gotten out of bed, potentially in the morning). In some examples, the smart watch 104 may be configured to provide progress updates at each interval of time since beginning the interaction at 106. At the time of each progress update, a dynamic messaging system may be configured to determine an appropriate message for the update. In some examples, the progress update may only present information about the user's best progress towards one or more activity goals. However, in other examples, the progress update may highlight the best progress, but also present other categories or progress information (e.g., in a less prominent fashion, like in smaller text, lower on the screen, and/or in a less visible shade).

In at least some embodiments, physical activities may be broken up into multiple categories. For ease of explanation, an example will be provided where activity categories include standing (e.g., calculated by determining a number of hours where the user 102 has stood for at least one minute), exercising (e.g., calculated by the number of minutes the user 102 has exercised), and moving (e.g., calculated by the number of calories burned by the user 102). For each of these categories, goals may be set by the user or by the developer. One example includes a stand goal of standing for at least one minute every hour of the day, an exercise goal of exercising at least 2.5 minutes for every hour of the day, and a move goal of burning 500 calories in a single day. Returning to the specifics of FIG. 1, the user 102 may begin interacting 106 with the smart watch 104 at 6:44 am. Additionally, the interval 108 for presenting progress updates may be set to four hours. As such, once the time interval 108 passes, a set of rules may be accessed to determine whether to provide a message and, if so, what to include in the message. In some examples, as desired, a rule may be in place that does not allow delivery of progress updates within twenty minutes before each hour and ten minutes after each hour. This rule may be in place to limit conflicts with a stand reminder (e.g., a reminder to the user 102 to stand up during the current hour) that may be configured to be presented at the end or beginning of each hour. So, while a progress update may been expected at 9:44 am (four hours after the user 102 began interaction with the smart watch 104), it may be delayed until 11:10 am, due to the stand reminder conflict rule. Thus, at 11:10 am, an interval-based message 110 may be presented by the smart watch 104, and the user 102 may have been interacting with the smart watch 104 for four full clock hours. The message 110 is interval-based because it is being presented based at least in part on the four hour interval setting, as opposed to a stand reminder or a goal completion message.

Once the dynamic message system determines that the smart watch 104 is to provide the interval-based message 110, it may determine what to include in the message. In some examples, the interval-based message 110 may include or highlight the "best" progress towards one of the goals described above. The following example facts may be used to illustrate an example calculation of a user's "best" progress. Assume that by 11:10 am (e.g., the time of the interval-based message 110), the user 102 has stood at least once (or for at least one whole minute) during three of the hour periods, the user 102 has exercised for a total of 11 minutes, and the user 102 has burned 197 calories. As such, the following calculations may be made:

To calculate the percentage of the user's stand goal completed:
  Stand goal currently completed is: 3 out of 12 hours.
  Perfect Stand goal completed for amount of time user has been wearing Watch: 4 out of 4 hours.
  Actual Stand goal achieved for amount of time user has been wearing Watch: 3 out of 4 hours possible.
  Success percentage for Stand goal so far: 75%.

To calculate the percentage of the user's exercise goal completed, assuming that the exercise goal could only be completed over the course of 12 hours at a flat rate of 2.5 exercise minutes per hour:
  Exercise goal currently completed is: 11 out of 30 minutes.
  Perfect Exercise goal completed for amount of time user has been wearing Watch: 10 out of 10 minutes (2.5 minutes per hour for 4 hours).
  Actual Exercise goal achieved for amount of time user has been wearing Watch: 11 out of 10 minutes possible.
  Success percentage for Exercise goal so far: 110%.

To calculate the percentage of the user's move goal completed, assuming that the move goal could only be completed over the course of 12 hours at a flat rate of the daily move goal divided by 12 hours:
  Move goal currently completed is: 197 out of 500 calories.
  Perfect Move goal completed for amount of time user has been wearing Watch: (500 calories/12 hours=47 calories per hour)×4 hours=167 calories.
  Actual Move goal achieved for amount of time user has been wearing Watch: 197 calories out of 167 possible.
  Success percentage of Move goal so far: 117%.

Thus, according to the above calculations, at 11:10 am, the stand goal success percentage would be 75%, the exercise goal percentage would be 110%, and the move goal percentage would be 117%. If the dynamic messaging system chose to present the highest percentage, then the interval-based message 110 would at least present the move goal percentage, along with its associated data and/or one or more comments regarding.

Once the interval-based message 110 has been provided, the next interval-based message may be scheduled based on the rules (in this case, four hours). In some examples, the user 102 may go for a run sometime after the interval-based message 110 (first progress update) is presented. The user 102 may, as a result of this exercise achieve one of their goals (e.g., exercise, move, run, steps, etc.) at 112. As such, even though the next interval-based message is not scheduled to be presented until 3:10 pm (four hours after the last one), a goal-based message 114 may be scheduled and presented based at least in part on the user 102 attaining the goal at 112. In this example, the goal-based message 114 may be presented at 1:32 pm, corresponding to the goal being achieved at 112. The goal-based message 114 may highlight the goal that was achieved (e.g., "100% of running goal achieved, congratulations!," or the like) and may include some additional information (e.g., it may present the progress rings, lines, or bars described above). Further, since the four hour time interval was interrupted by the goal-based message 114, the dynamic messaging system may be configured to start the time interval over again to avoid sending the user 102 too many messages. As such, the time interval 116 (e.g., four hours) may pass before the next message. In this example, that would mean that the next interval-based message 118 might be presented at 5:32 pm (four hours from the last goal-based message 114)

While various examples are illustrated and explained with reference to FIG. 1, it should be understood that these are just a few of many variations of times, messages, physical activity goals and/or categories, or the like that may be possible with the dynamic messaging system described herein. Additionally, while most of these examples have been provided with reference to a smart watch 104, any of the data may be stored, processed, and/or provided by one or more service providers (e.g., a web service or the like) hosted by one or more servers accessible by the smart watch 104 over one or more networks.

Figure 2:
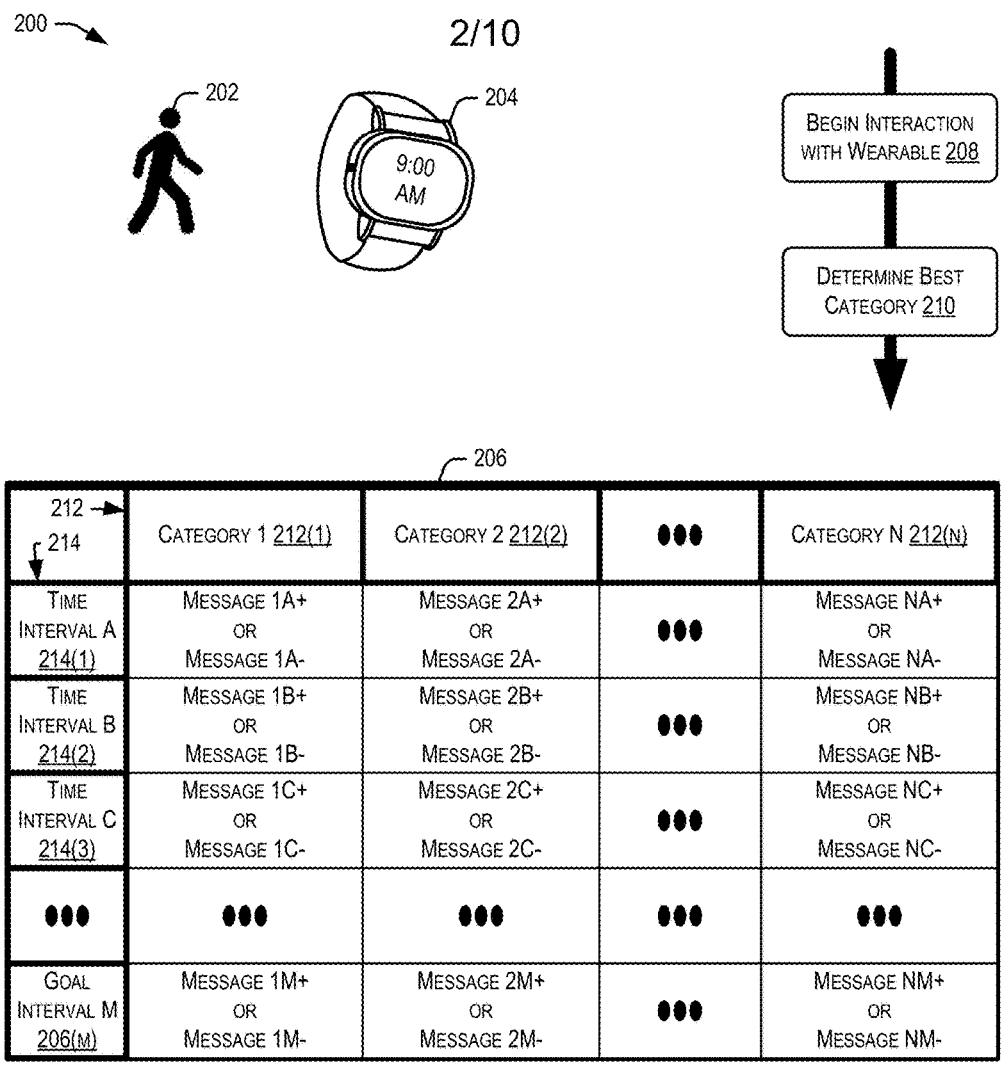
FIG. 2 is another simplified block diagram illustrating at least some example techniques for providing dynamic rule-based messages as described herein, according to at least one example.
Figure 2:
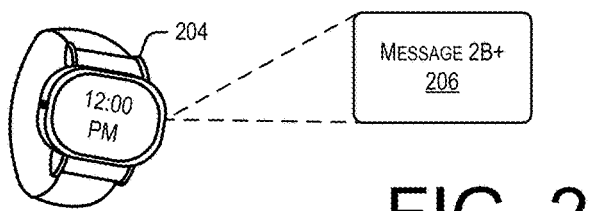

FIG. 2 illustrates another workflow 200 that shows additional example implementations of the dynamic messaging system described herein, where a user 202 may interact with any wearable device (e.g., a smart watch) 204. Additionally, FIG. 2 illustrates one example grid 206 (graph, table, or the like) for determining an appropriate message to present on the smart watch 204. For example, as noted, the dynamic messaging system may be configured to present different messages based at least in part on a time interval and/or a user's progress towards a goal. As such, the determination of which message to present may be defined by one or more rules (e.g., stored in the grid 206). In this workflow 200, the user 202 may begin interacting with the smart watch 204 at 208 (e.g., at 9:00 am). Additionally, at 210, the system may determine a "best" category (e.g., calculated using the example described above).

The table 206 may include a top row 212 labeled "Category 1" 212(1), "Category 2" 212(2), through "Category N" 212(N), where N is some positive integer. These categories 212 may correspond to any number of different physical activity categories, as described above. Additionally, the table 206 may include a first column 214 labeled "Time Interval A" 214(2), "Time Interval B" 214(2), "Time Interval C" 214(3), through "Time Interval M" 214(M), where M is some positive integer. The time intervals 214 may correspond to particular hours of a day (e.g., 10:00 am, 11:00, am, etc.), hour ranges of a day (6:01 am-10:00 am, 10:01 am-2:01 pm, etc.), days of week (e.g., Monday, Tuesday, etc.), or any other time interval over a total time period, as desired. In some examples each cell of the grid 206 may include one or more messages that may be presented, depending on the particular factors. The messages may be labeled with a "+" or "−" to indicate particular messages that are intended for situations when the user is above or below their goal for that particular category 212 and time interval 214 pair. For example, "Message 1A+" might be presented for "Category 1" 212(1) during "Time interval A" 214(1) when the user is above their goal for that category. As described above, being above a goal may be calculated based on collected physical activity information of the user and particular factors associated with the category. Similarly, "Message 1A−" might be presented for "Category 1" 212(1) during "Time Interval A" 214(1) when the user is below their goal for that category.

In some examples, once the best category is determined at 210 (e.g., a progress update is scheduled to be presented, and the system determines to highlight the user's progress towards a goal), the system may access the grid 206 to identify an appropriate message to be presented. In one example, "Category 2" 212(2) may be the exercise goal, and the system may have determined at 210 that the user's progress towards their exercise goal is the best (e.g., has the best percentage). As such, the system may determine the current time falls within "Time Interval C" 214(3), and then may access the cell in the grid 206 that corresponds to 212(2)×214(3). That cell may include one or more messages that the system may choose from depending on the particular factors. For example, that cell may include at least "Message 2C+" and "Message 2C−." The "+" message may be used when the user is above their goal, while the "−" message may be used when the user is below their goal. Alternatively, or in addition, the "+" message may be used when the user is above some threshold (that may be below the goal, e.g., 50% of the goal, or the like), while the "−" message may be used when the user is below that threshold (e.g., 75% of the goal, or the like).

Figure 3:
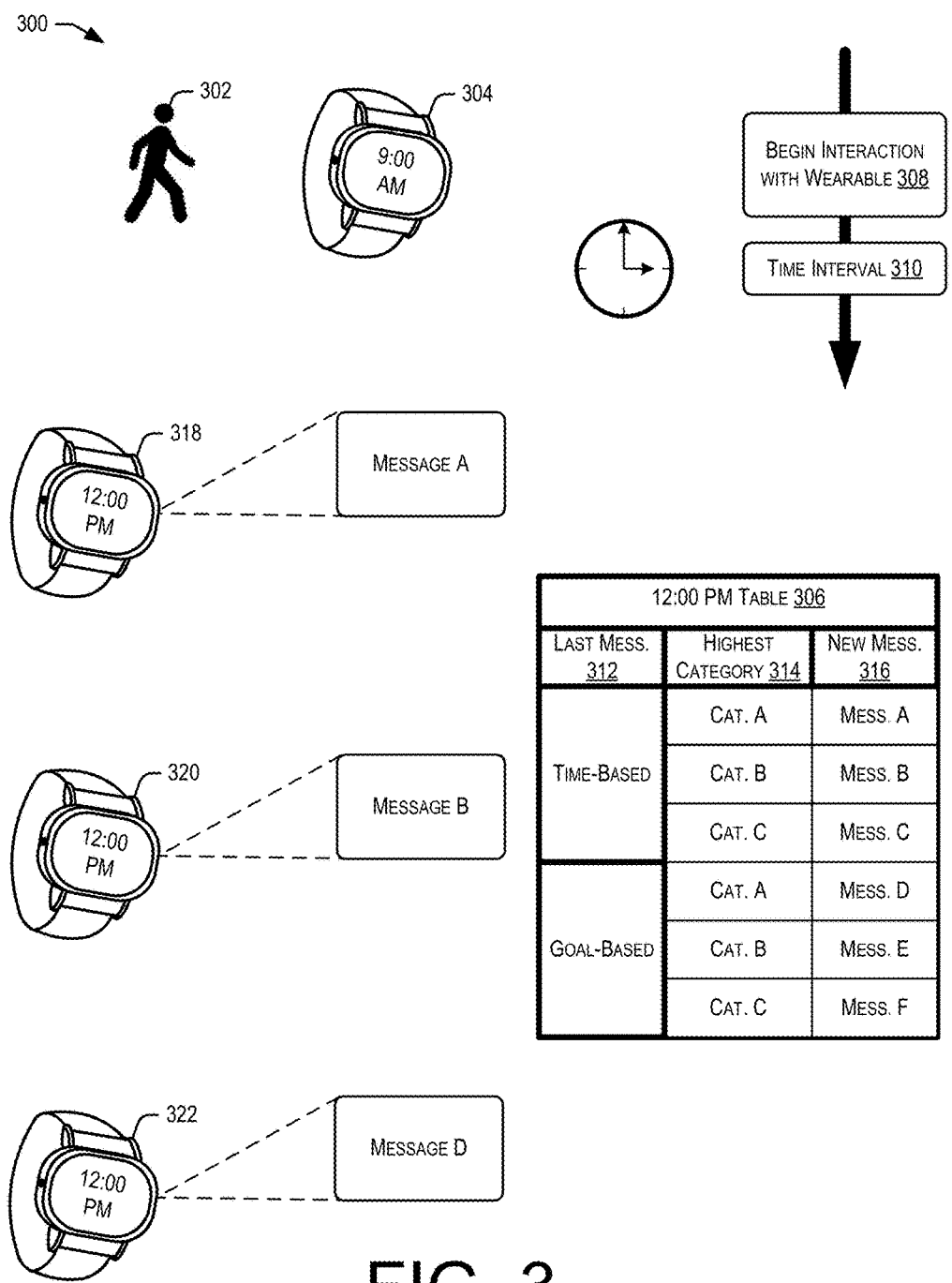
FIG. 3 is another simplified block diagram illustrating at least some example techniques for providing dynamic rule-based messages as described herein, according to at least one example.

FIG. 3 illustrates another workflow 300 that shows additional example implementations of the dynamic messaging system described herein, where a user 302 may interact with any wearable device (e.g., a smart watch) 304. Additionally, FIG. 3 illustrates one example grid 306 (graph, table, or the like) for determining an appropriate message to present on the smart watch 304. For example, as noted, the dynamic messaging system may be configured to present different messages based at least in part on a time interval, a user's progress towards a goal, and/or what message was presented last. As such, the determination of which message to present may be defined by one or more rules. In some examples, the rules may be stored within the grid 306; however, in other examples, the rules may define how to read or utilize the grid 306 to identify the appropriate message to provide. In this workflow 300, the user 302 may begin interacting with the smart watch 304 at 308 (e.g., at 9:00 am). Additionally, at 310, the system may determine that the time interval has expired, thus indicating that it is time to present the next time-based message.

The grid 306 may be for a particular time of the day or a particular interval of any given period (e.g., days of the week, or the like). In this example, for the sake of explanation, the table 306 is associated with 12:00 pm. In some examples, a separate table may exist for each time interval and/or for each particular time (e.g., of a day, or the like). The table 306 may also have columns that identify the "last message" provided 312, the "highest category" identified for the user 314, and/or the "new message" to be provided 316. In some examples, once the time interval expires at 310, the system may determine what type of message was provided last and what the highest category is for the user. A corresponding cell within the table 306 may then be accessed. This corresponding cell may provide a rule for the system to follow and/or may provide the message to be presented. Three different example smart watches 318, 320, 322 are illustrated here for showing three different examples at 12:00 pm.

In one of the three examples, the system may determine that the user's progress towards category A is the best. Additionally, the system may check the last message provided, and determine that it was a time-based message (progress update) as opposed to a goal-based message. In some cases, this means that no new goals have been attained since the last message. In grid 306, "Message A" is the new message 316 that corresponds to the last message 312 being time-based and the highest category 314. As such, "Message A" may be prepared for presentation (or presented) on the wearable device 318. In another example, if the last message 312 was a time-based message, but the highest category 314 is category B, then the new message 316 may be "Message B." However, in other examples, at 12:00 pm, it may be determined that the last message 312 was a goal-based message. Thus, even if the highest category 314 is still category A, the new message 316 may be different (e.g., here, it would "Message D"). In some embodiments, the main difference between "Message A" and "Message D," which both correspond to category A being the highest category 314 at 12:00 pm, may be that "Message D" follows a goal-based message, while "Message A" follows a time-based message. In some cases, this may be because the goal-based message may have provided information that the system does not want to repeat in the new message. Thus, while "Message A" might indicate that the user is progressing the most in category A, "Message D" might indicate the user's second best category (instead of category A), since the previous goal-based message may have already indicating that the goal for category A was just recently achieved.

Sample time-based messages at 12:00 pm, when a goal is not close to being attained, may include "Throughout your day, take breaks from sitting to reach your stand goal," "Accumulate 30 minutes of brisk activity to hit your exercise goal. You can do this," and "Keep moving to stay on pace towards today's move goal." Sample time-based messages at 12:00 pm, when a goal is closer to half complete, may include "Keep it up. It's still early and you're X % of the way to your stand goal," "Nice progress towards your exercise goal. You're X % of the way there," and "You're X % of the way to your move goal. Keep it going." Sample time-based messages at 12:00 pm, when a goal is nearly complete, may include "You're making fantastic progress towards your goal. Only Y more stand hours to go," "Way to push it this morning. You're already only Y minutes from your exercise goal," and "You're only Y calories away from your move goal, and it's only noon. Keep it up." As noted, at different times of the day, and for different levels of goal completion, the messages may include different information and/or have different tones. For example, closer to the evening, if a user is not close to completing a goal, sample messages may include "Go for it this evening and you may be able to hit your goal."

Figure 4:
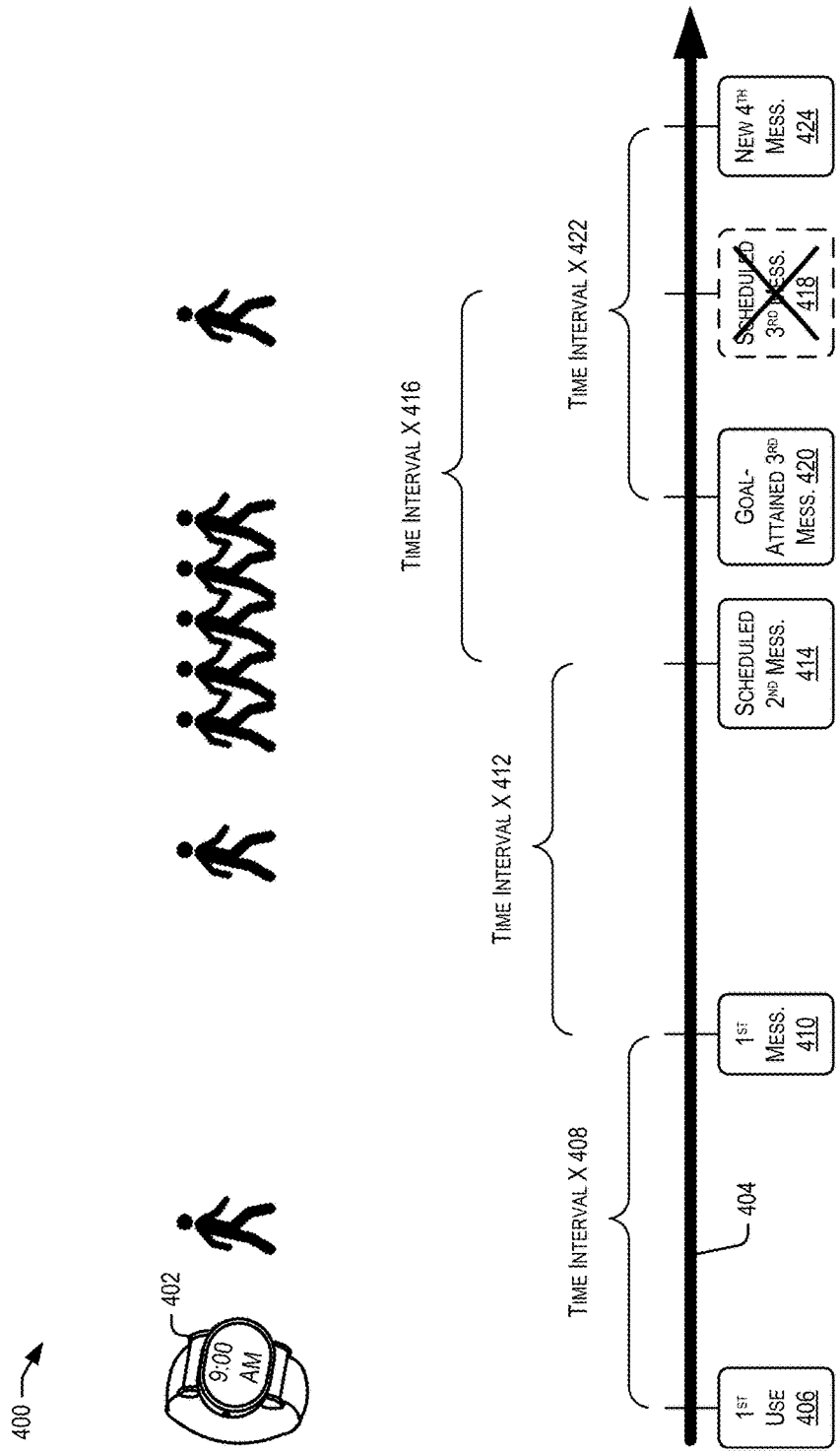
FIG. 4 is another simplified flow diagram illustrating at least some example techniques for providing dynamic rule-based messages as described herein, according to at least one example.

FIG. 4 illustrates an example flow 400 for determining when to provide a next message, using the dynamic messaging system described herein. In some examples, a user may begin interacting with a wearable device (e.g., a smart watch) 402 (e.g., at 9:00 am). On the timeline 404, this is indicated as the "first use" 406. After the "first use" 406, the time interval X 408 may begin and the user may be going about his regular daily business. The time interval X 408, may be any amount of time, as desired, and may be set by the user or configured by an administrator or developer of the system. Additionally, the system may determine an optimal time interval or desired interval based at least in part on historical activity information of the user. For example, if the user typically only achieves 30% of their goals, each day, the system may learn (e.g., using one or more machine learning techniques) that longer time intervals are better. That is, a longer time interval may give the user more time to get closer to his goals, and may make it so less messages are provided throughout the day. This may be desired because, for a user that is not regularly meeting their goals, having constant reminders of this may be discouraging.

At the end of the time interval X 408, a first message 410 may be presented to the user. As noted, the message may indicate some physical activity information of the user, including but not limited to progress towards one or more goals, a highlighted category or goal that the user is excelling at, or the like. Once the first message 410 has been presented, a second time interval X 412 may begin. Once the second time interval X 412 begins, a second message 414 may be scheduled. The second message 414 is indicated as scheduled, because if nothing changes, the second message 414 should be presented at the end of the second time interval 412. At some time around when the second message 414 is presented, the user may exercise (e.g., they may go for a run, a long walk, or the like). As such, even though the third time interval X 416 has begun, and the third message 418 has been scheduled, the user may attain one of their goals. In some examples, one of the rules of the system may be that intervals and/or interval-based messages (progress updates) can be interrupted when a user attains a goal. As such, instead of waiting for the scheduled third message 418, the system may interrupt the third time interval X 416 to present the goal-attained third message 420. This goal-attained third message may effectively replace the scheduled third message 418 and a new (fourth) time interval X 422 may begin. Now, since the third time interval 416 was interrupted by the goal-attained third message 420, the system may be configured to completely skip the scheduled third message 418 and ignore the third time interval X 416 altogether. In this way, the user is not presented with a time-based interval (message 418) just after receiving the goal-attained third message 420. This is desired, in part, because the goal-attained message 420 may also include some progress update information (e.g., the user's progress towards other goals, as well as the attained goal). Thus, the user does not need to receive that information again (e.g., shortly after the goal-attained message 420). Instead, a new, fourth time interval X 422 may have begun at the time the goal-attained message 420 was presented. If nothing changes (e.g., no other goals are attained during the fourth time interval X 422), the system may then provide a new, fourth message 424 at the end of the fourth time interval X 422. Additionally, in some cases, when a new interval is started before a previous one finishes (e.g., a goal-attained message was provided during a time interval), the next message may also include different information than it would have otherwise. In other words, it may not only be the timing of the messages that change, but also the messages themselves.

Figure 5:
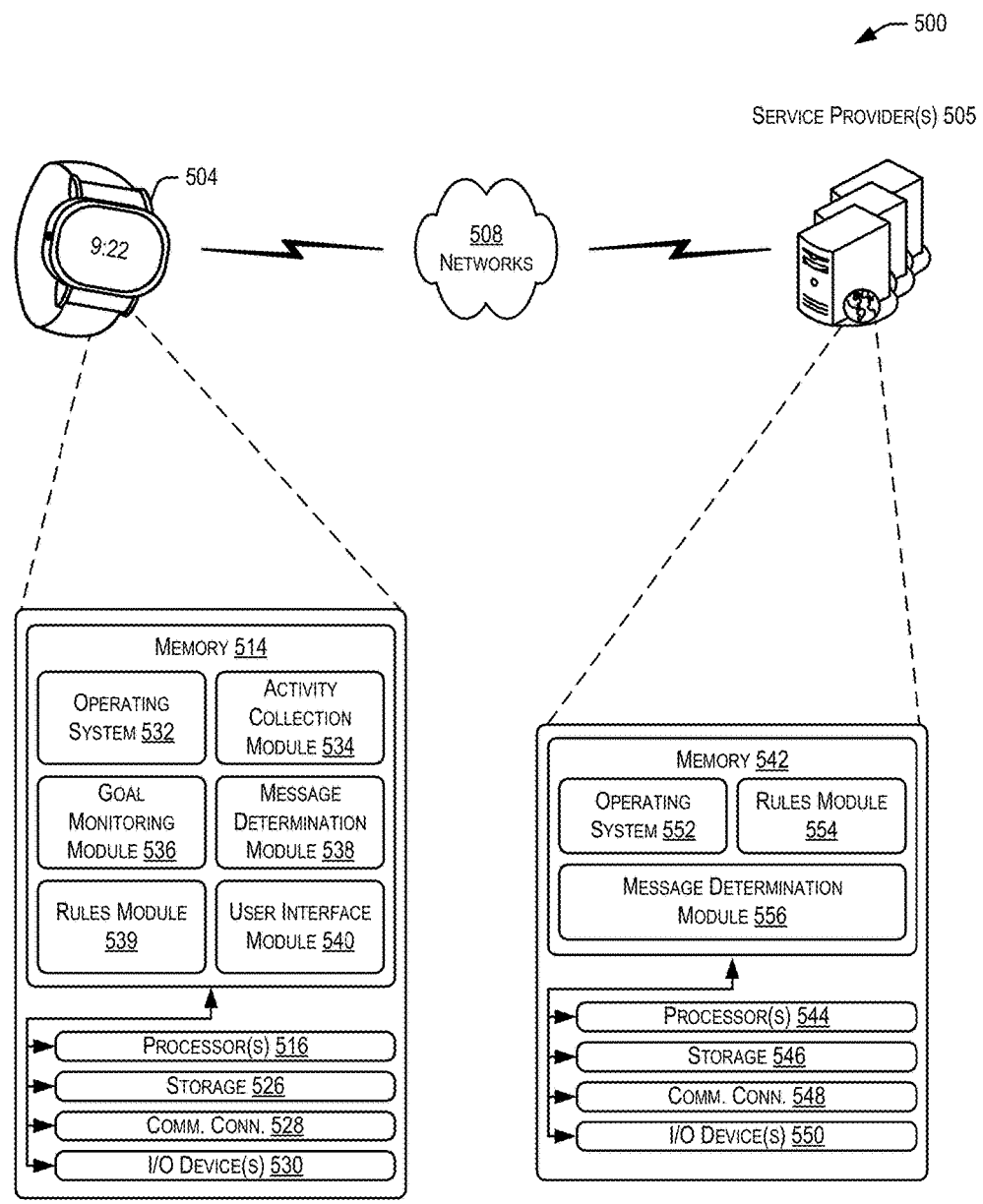
FIG. 5 is a simplified architecture diagram illustrating at least some example techniques for providing dynamic rule-based messages as described herein, according to at least one example.

FIG. 5 illustrates an example architecture or environment 500 configured to determine, provide, and/or present dynamic messages on wearable device 504 (e.g., a smart watch), according to at least one example. In some examples, the example architecture 500 may further be configured to manage or otherwise interact with one or more service providers and/or service provider computers 505 or other computing devices of FIG. 1 (e.g., a cellular provider and/or a web service provider). In some examples, the devices may be connected via one or more networks 508 (e.g., via Bluetooth, WiFi, the Internet, or the like). In the architecture 500, one or more users may utilize the wearable device 504 to track physical activity of the user.

In some examples, the smart watch 504 (when physically worn by the user) may be configured to collect or otherwise detect user activity and/or behavior information. For example, the smart watch 504 may be able to identify whether the user is walking, running, lying down, sleeping, standing, or the like. Thus, the smart watch 504 may be able to identify activity and/or behavior of the user throughout a period of time. In some examples, the activity information may be received by provided to the service provider computers 505 (e.g., from the smart watch 204). The service provider computers 505 may then be able to store and/or process the information to determine the appropriate messages to be provided.

In some examples, the networks 508 may include any one or a combination of many different types of networks, such as cable networks, the Internet, wireless networks, cellular networks, satellite networks, other private and/or public networks, or any combination thereof. While the illustrated example represents the wearable device 504 accessing the service provider computers 505 via the networks 508, the described techniques may equally apply in instances where the wearable device 504 interacts with the service provider computers 505 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the wearable device 504 may be configured to execute or otherwise manage applications or instructions for operating one or more biometric sensors, motion detection sensors, or other sensor devices configured to identify user activity. The wearable device 504 may collect such physical activity information and compare it against one or more activity goals, for one or more activity categories. Based on a set of rules, the time of day (or some other period), the user's progress towards those goals, and/or what information was provided in previous messages, the wearable device 504 and/or the service provider computers 505 may determine one or more dynamic messages to be presented to the user. The wearable device 504 may then present these messages to the user (e.g., through a UI or other interface).

The wearable device 504 and/or the service provider computers 505 may be any type of computing device such as, but not limited to, a mobile phone, a smartphone, a personal digital assistant (PDA), a laptop computer, a desktop computer, a thin-client device, a tablet computer, a smart watch, a wireless headset, or the like. As noted, the service provider computers 505 may be in communication with the wearable device 504 via the networks 508, or via other network connections.

In one illustrative configuration, the wearable device 504 may include at least one memory 514 and one or more processing units (or processor(s)) 516. The processor(s) 516 may be implemented as appropriate in hardware, computer-executable instructions, firmware, or combinations thereof. Computer-executable instruction or firmware implementations of the processor(s) 516 may include computer-executable or machine-executable instructions written in any suitable programming language to perform the various functions described. The wearable device 504 may also include accelerometer devices and/or motion detection device for detecting a user's activity or motion while wearing the wearable device 504 or while the user is within view of the wearable device 504. The wearable device 504 may also include geo-location devices (e.g., a global positioning system (GPS) device or the like) for detecting, providing, and/or recording geographic location information associated with the wearable device 504 and/or the user.

The memory 514 may store program instructions that are loadable and executable on the processor(s) 516, as well as data generated during the execution of these programs. Depending on the configuration and type of the wearable device 504, the memory 514 may be volatile (such as random access memory (RAM)) and/or non-volatile (such as read-only memory (ROM), flash memory, etc.). The wearable device 504 may also include additional removable storage and/or non-removable storage 526 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 514 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 514 and the additional storage 526, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 514 and the additional storage 526 are both examples of non-transitory computer storage media. Additional types of computer storage media that may be present in the wearable device 504 may include, but are not limited to, phase-change RAM (PRAM), SRAM, DRAM, RAM, ROM, electrically erasable programmable read-only memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the wearable device 504. Combinations of any of the above should also be included within the scope of non-transitory computer-readable storage media.

Alternatively, computer-readable communication media may include computer-readable instructions, program modules, or other data transmitted within a data signal, such as a carrier wave, or other transmission. However, as used herein, computer-readable storage media does not include computer-readable communication media.

The wearable device 504 may also contain communications connection(s) 528 that allow the wearable device 504 to communicate with a data store, another computing device (e.g., the user device 502) or server, user terminals and/or other devices via the networks 508. The wearable device 504 may also include I/O device(s) 530, such as a keyboard, a mouse, a pen, a voice input device, a touch input device, a display, speakers, a printer, etc. For example, utilizing a speaker and microphone, the wearable device 504 may be configured to answer an incoming telephone call.

Turning to the contents of the memory 514 in more detail, the memory 514 may include an operating system 532 and/or one or more application programs or services for implementing the features disclosed herein including an activity collection module 534, a goal monitoring module 536, a message determination module 538, a rules module 539, and/or a user interface module 540. In some examples, the activity collection module 534 may be configured to detect user actions and store associated physical activity information. For example, and as discussed above, one or more sensors of the wearable device 504 may be able to detect actions of the user. In some examples, the activity collection module 534 may be configured to determine and/or associate one or more categories with the activity information. Some user actions may cover multiple categories, for example, a step by the user may indicate that the user is standing (covering the stand category), walking (covering the walk category), burning calories (covering the calorie burning category), or the like all at the same time for the same action. The activity information and associated metadata (e.g., the respective categories, time of activity, etc.) may be stored by the activity collection module 534 in the memory 514 or other memory of the wearable device 504. The activity collection module 534, in some examples, may also transmit the information to the service provider computers 505.

The goal monitoring module 536, in some cases, may be configured to monitor one or more goals of the user, and track the user's progress with respect to the activity information collected by the activity collection module 534. In some cases, the goal monitoring module 536 may also receive user configuration or setting information for setting the goal itself (e.g., received from the user interface module 540). In some examples, the goals may be set to a default value, that can be configured or otherwise changed by the user, a developer, or an administrator (e.g., a coach). The default goal values may be the initial settings when the user begins using the wearable device 504 or the goal monitoring module 536 may be configured to reset the goal values back to the default values after a certain amount of time, at the request of a user, based on some triggering event, and/or randomly. Additionally, the goal monitoring module 536 may be configured to automatically determine an appropriate goal value for each category.

The message determination module 538 may be configured to determine the appropriate dynamic messages to present via the wearable device 504 (e.g., to the user). As such, the message determination module 538 should be able to check the current time, it should have access to the activity information collected by the activity collection module 534, and it should have access to the goals stored and/or monitored by the goal monitoring module 536. Additionally, the message determination module 538 should be able to access the set of rules managed by the rules module 539. In some cases, the rules module 539 may be configured to store, update, and/or delete the rules (e.g., in a data structure such as a table, grid, or the like). The rules module 539 may also be configured to access a database that stores the rules.

The user interface module 538 may be configured to manage the user interface of the wearable device 504. For example, the user interface module 538 may present the generated (or looked-up) messages in such a way that the user can review them. The user interface module 538 also be configured to present one or more UI objects (e.g., rings, bar graphs, lines, etc.) that represent a visual depiction of the user's progress towards their goals. Further, the user interface module 538 may provide, for display, one or more options for updating the goals or goal values of the user. Additionally, in some examples, the user interface module 538 may be configured to receive and/or interpret user gesture information (e.g., via touch screen) for updating the goal information and/or for dismissing, snoozing, or otherwise interacting with the messages. For example, a user may swipe an alert of the wearable device 504 that indicates that the message has been reviewed. As desired, the user interface module 538 may also be utilized to provide other alerts and/or other notifications regarding the wearable device 504 (e.g., current settings).

While many of the examples herein are described with reference to the wearable device 504 being a smart watch, it should be understood that any type of computing device may be used to perform the functions/embodiments described, as appropriate. For example, the wearable device 504 may be a wireless headset or earpiece, or other computing device that can collect user activity information (e.g., including an accelerometer or other motion detection device). Where the wearable device 504 is a wireless headset or earpiece, the wearable device 504 may also be equipped a microphone and speaker(s). As such, the wearable device 504 (as described above) may be configured for answering incoming phone calls on behalf of a user device (e.g., a mobile phone).

The service provider computers 505 may also be any type of computing device. In one illustrative configuration, the service provider computers 505 may include at least one memory 542 and one or more processing units (or processor(s)) 544. The processor(s) 544 may be implemented as appropriate in hardware, computer-executable instructions, firmware, or combinations thereof. Computer-executable instruction or firmware implementations of the processor(s) 544 may include computer-executable or machine-executable instructions written in any suitable programming language to perform the various functions described.

The memory 542 may store program instructions that are loadable and executable on the processor(s) 544, as well as data generated during the execution of these programs. Depending on the configuration and type of the service provider computers 505, the memory 542 may be volatile (such as RAM) and/or non-volatile (such as ROM, flash memory, etc.). The service provider computers 505 may also include additional removable storage and/or non-removable storage 546 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 542 may include multiple different types of memory, such as SRAM, DRAM, or ROM. While the volatile memory described herein may be referred to as RAM, any volatile memory that would not maintain data stored therein once unplugged from a host and/or power would be appropriate. The memory 542 and the additional storage 546, both removable and non-removable, are both additional examples of non-transitory computer-readable storage media.

The service provider computers 505 may also contain communications connection(s) 548 that allow the service provider computers 505 to communicate with a data store, another computing device or server, user terminals and/or other devices via the networks 508. The service provider computers 505 may also include I/O device(s) 550, such as a keyboard, a mouse, a pen, a voice input device, a touch input device, a display, speakers, a printer, etc.

Turning to the contents of the memory 542 in more detail, the memory 542 may include an operating system 552 and/or one or more application programs or services for implementing the features disclosed herein including a rules module 554 and/or a message determination module 556. In some examples, the rules module 554 may be configured to manage and/or update the rules for determining what messages to provide to users and when. For example, the rules module 554 may operate much like the rules module 539 of the wearable device 504, except for instances when the service provider computers 505 are expected to do the computation and determination of the dynamic messages to provide to the user. In other words, the service provider computers 505 may act as a sort of web service that the wearable device 504 can, on occasion, call on (e.g., utilizing one or more application programming interface (API) method calls) to act as the dynamic messaging system on behalf of the wearable device 504. In that case, the wearable device 504 may provide the collected activity information, the rules, the goals, etc. of the user to the service provider computers 505. Similarly, the message determination module 556 may be configured to aid in the service provider computers 505 ability to act as a web service in that it may be configured to utilize the information collected, stored, and/or provided by the wearable device 504 to determine the appropriate messages to be presented via the wearable device 504. In that case, the service provider computers 505 may then provide the appropriate messages back to the wearable device 504 for presentation to the user via the wearable device (e.g., utilizing the user interface module 540).

Figure 6:
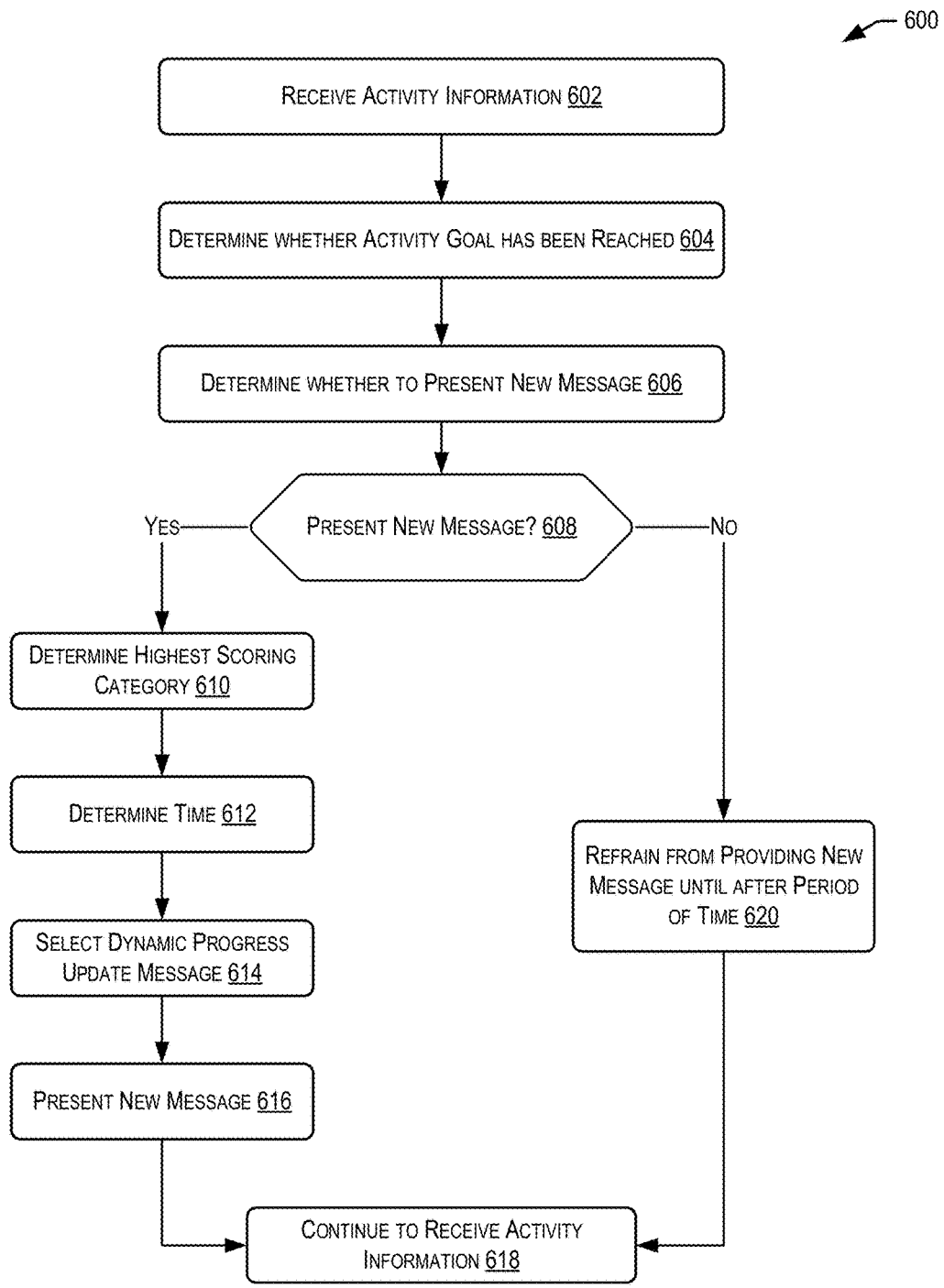
FIG. 6 is another simplified flow diagram illustrating an example process for providing dynamic rule-based messages as described herein, according to at least one example.
Figure 7:
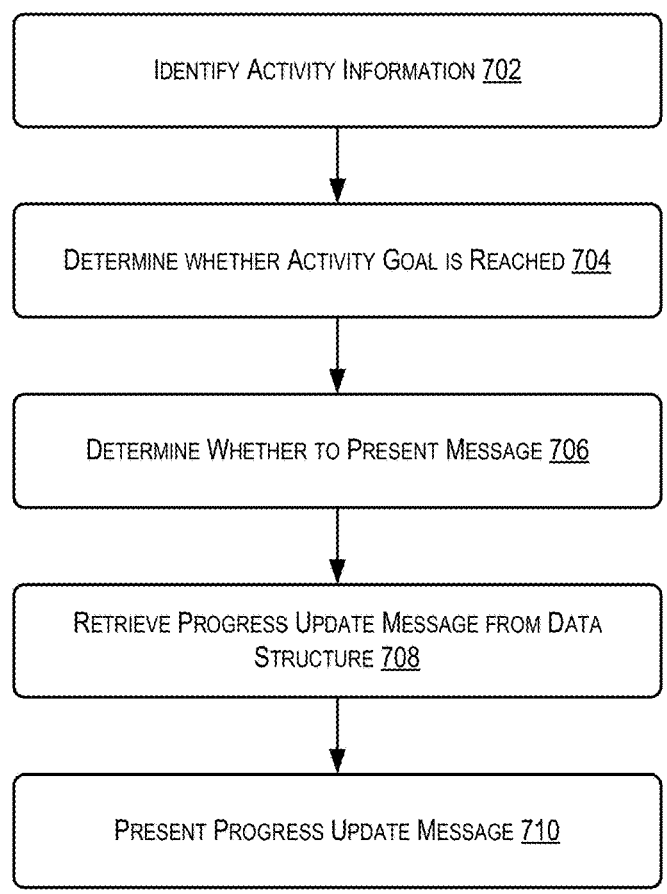
FIG. 7 is another simplified flow diagram illustrating another example process for providing dynamic rule-based messages as described herein, according to at least one example.

FIGS. 6 and 7 illustrate example flow diagrams showing respective processes 600 and 700 for managing dynamic messages, as described herein. These processes 600 and 700 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

In some examples, the wearable device 504 of FIG. 5 (e.g., utilizing at least the activity collection module 534, the message determination module 538, and/or the rules module 539 shown in FIG. 5), or any other wearable device described here, may perform the process 600 of FIG. 6. The process 600 may begin at 602 where a user device may receive activity information. The activity information may be associated with a user and may belong to one or more activity categories. At 604, the user device may determine whether an activity goal of the user has been reached. In some cases, if an activity goal has been reached, the user device may present a message that indicates the attainment of the goal, and the user device may go back to receiving activity information at 602. A new interval may be started, as desired. However, if no activity goal has been reached, the user may device may proceed to determining whether to present a new message at 606. This determination may be based at least in part on how long it's been since the last message, as well as other factors or rules that govern the messaging system. At 608, the user device may proceed to determining a highest (best) activity score at 610. Several different calculations may be utilized for determining a user's best scoring category including, but not limited to, determining which goal category is closest to being completed in the remaining period under review (e.g., the day), determining which goal will likely be completed, determining towards which activity category the use has made the most progress.

At 612, still in the scenario where it was determine to present a new message, the user device may determine a current time (e.g., the time of day, a day of the week, etc.). At 614, the user device may select a dynamic progress update message to be provided to the user. This selection may be performed by looking up a rule or message in a table based at least in part on the factors described above. At 616, the user device may present the new message to the user. However, if these operations were performed by the a service provider, instead of the user device, the service provider may provide the new message to the user device at 616. The user device may then continue to receive activity information at 618 or return to 610. Alternatively, in some examples, the user device may determine not to present (or provide) the new message at 608, in which case the user device may refrain from presenting the new message until after a period of time at 620. For example, the period of time might be one or more time intervals (e.g., the time interval used to identify when to present the time-based messages or the like).

FIG. 7 illustrates another process 700 for providing dynamic messages, according to at least a few embodiments. In some examples, the wearable device 504 of FIG. 5 (e.g., utilizing at least the activity collection module 534, the message determination module 538, and/or the rules module 539 shown in FIG. 5), or any other wearable device described here, may perform the process 700 of FIG. 7. The process 700 may begin at 702 where the user device may identify activity information of the user. At 704, the user device may determine whether an activity goal has been reached. For example, activity progress of the user may be tracked against an activity goal for one or more categories. As such, for each category, the user device may determine whether a goal of one of the categories has recently been reached. At 706, the user device may determine whether to present a message. As noted, this determination may be based on the time of day, the user's progress towards their goals, what message was provided last, whether the current time is within a timeframe excluded from providing messages (e.g., a few minutes before and after each hour, etc.). At 708, the user device may retrieve progress update message from a data structure. For example, the user device may refer to one or more rules that may be stored in a data structure such as a table, grid, or spreadsheet. At 710, the user device may present a progress update message to a user (e.g., when a goal has been reached).

Figure 8:
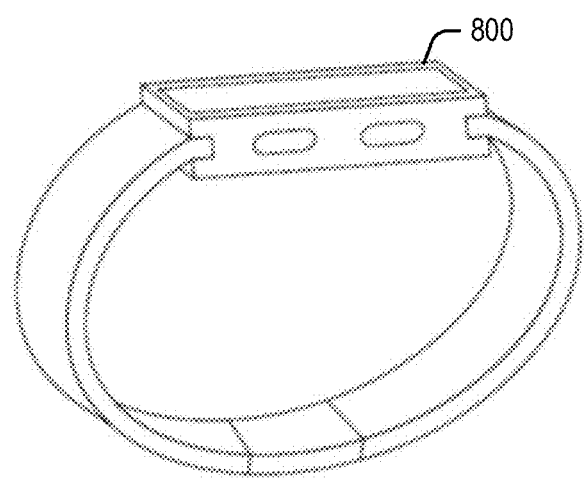
FIG. 8 is a simplified block diagram illustrating an example device for providing dynamic rule-based messages as described herein, according to at least one example.

Embodiments described herein may take the form of, be incorporated in, or operate with a suitable electronic device. One example of such a device is shown in FIG. 8 and takes the form of a wearable mechanism 800 (e.g., the wearable device 504 of FIG. 5 or another type of smart device). As shown, the mechanism may be worn on a user's wrist and secured thereto by a band. The mechanism may have a variety of functions including, but not limited to: keeping time; monitoring a user's physiological signals and providing health-related information based at least in part on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative embodiments of suitable electronic devices include a mobile phone, a tablet computing device, a portable media player, and so on. Still other suitable electronic devices may include laptop/notebook computers, personal digital assistants, touch screens, input-sensitive pads or surfaces, and so on.

Figure 9:
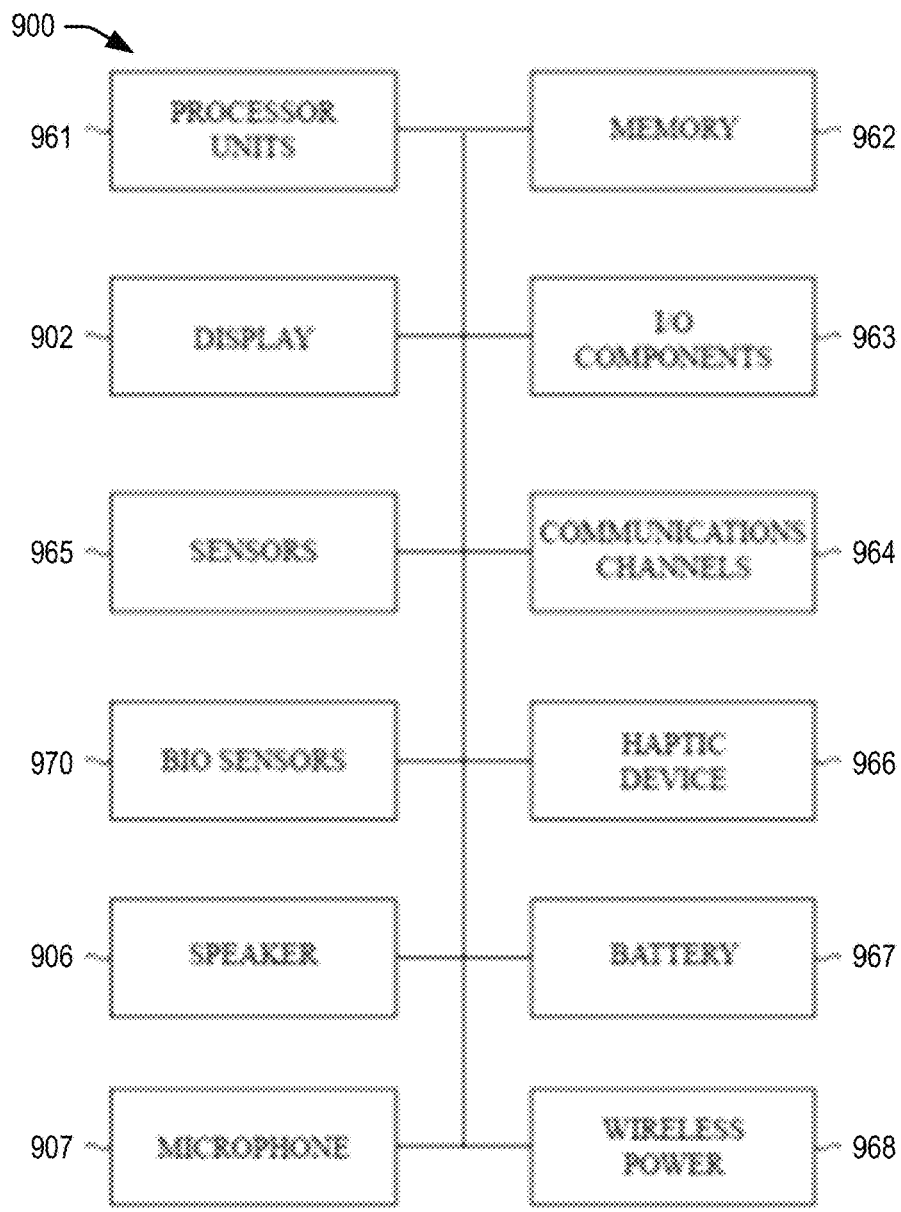
FIG. 9 is a simplified block diagram illustrating another example architecture for providing dynamic rule-based messages as described herein, according to at least one example.

FIG. 9 depicts an example schematic diagram of a wearable electronic device 900. As shown in FIG. 9, the device 900 includes one or more processing units 961 that are configured to access a memory 962 having instructions stored thereon. The instructions or computer programs may be configured to perform one or more of the operations or functions described with respect to the device 900. For example, the instructions may be configured to control or coordinate the operation of the various components of the device. Such components include, but are not limited to, display 902, one or more input/output components 963, one or more communication channels 964, one or more sensors 965, a speaker 906, microphone 907, and/or one or more haptic feedback devices 966. In some embodiments the speaker and microphone may be combined into a single unit and/or may share a common port through a housing of the device.

The processing units 961 of FIG. 9 may be implemented as any electronic device capable of processing, receiving, or transmitting data or instructions. For example, the processing units 961 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

In some embodiments the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some embodiments, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such embodiments the band may include electrical interconnections that permit the two devices to transmit signals to one another and thereby interact with one another.

In many embodiments, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments.

The device 900 also may comprise one or more touch sensors to determine a location of a touch on the cover glass. A touch sensor may be incorporated into or on the display stack in order to determine a location of a touch. The touch sensor may be self-capacitive in certain embodiments, mutual-capacitive in others, or a combination thereof.

Similarly, the device 900 may include a force sensor to determine an amount of force applied to the cover glass. The force sensor may be a capacitive sensor in some embodiments and a strain sensor in other embodiments. In either embodiment, the force sensor is generally transparent and made form transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

The electronic device 900 may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic and/or visual components of the alert may be synchronized to provide an overall experience to a user. One or more components may be delayed relative to other components to create a desired synchronization between them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output but at a weak or even subliminal level, thereby priming the wearer to receive the auditory output.

The example electronic device 900 may communicate with other electronic devices either through a wired connection or wirelessly. Data may be passed between devices, permitting one device to relay information to another; control another; employ another's sensors, outputs, and/or inputs; and so on.

Figure 10:
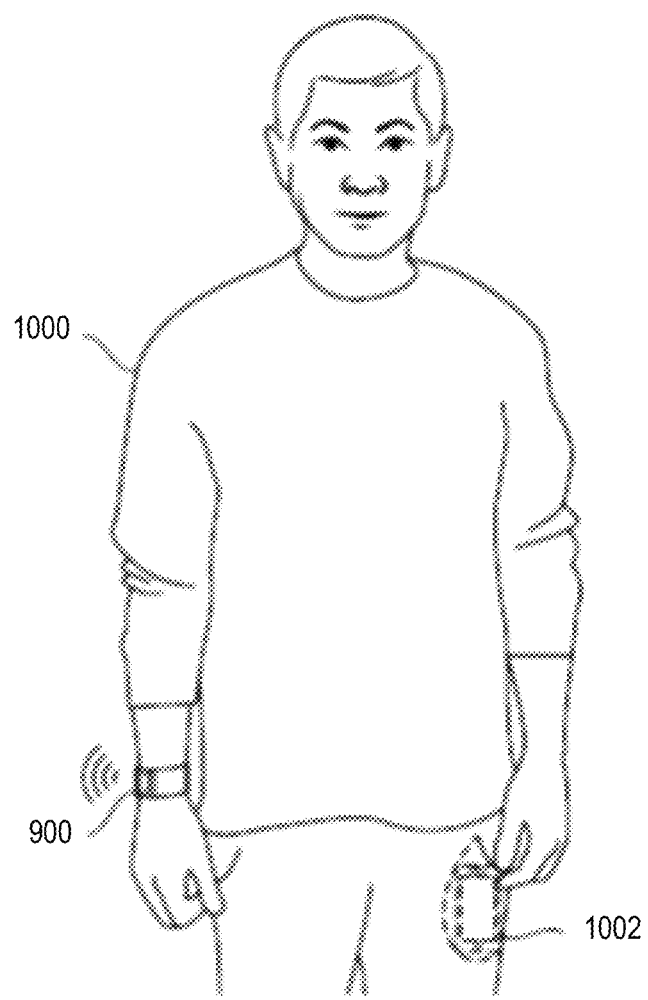
FIG. 10 is a simplified block diagram illustrating additional example devices for providing dynamic rule-based messages as described herein, according to at least one example.

FIG. 10 depicts a user 1000 wearing a sample wearable electronic device 900 with a second (e.g., portable) electronic device 1002 in his pocket. Data may be wirelessly transmitted between the electronic devices 900, 1002, thereby permitting the user 1000 to receive, view, and interact with data from the second device 1002 by means of the first electronic device 900. Thus, the user 1000 may have access to part or all of the second device's functionality through the first electronic device 900 without actually needing to interact directly with the second device 1002.

Further, the electronic devices 900, 1002 may cooperate not only to share data but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access and the like between the two and ultimately to a user. As one non-limiting example, the electronic device 900 may be unable to place or receive telephone calls while the second device 1002 may be able to do so. A user may nonetheless make and/or receive calls through the first device 900, which may employ the second device 1002 to actually place or accept a call.

As another non-limiting example, an electronic device 900 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain embodiments may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health information to be provided to a user. In some examples, the sensed biometric information may be used by the alert manager, in part, for managing the electronic content and/or the incoming alerts.

Certain embodiments may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems also may be used (e.g., near field magnetic resonance and radio frequency). Alternatively, the device also may employ wired charging through electrodes.

In certain embodiments, the device may include a rotary input, which may take the form of a crown with a stem. The crown and stem may be rotated to provide the rotary input. Rotation of the stem and/or crown may be sensed optically, electrically, magnetically, or mechanically. Further, in some embodiments the crown and stem may also move laterally, thereby providing a second type of input to the device.

The electronic device may likewise include one or more buttons. The button(s) may be depressed to provide yet another input to the device. In various embodiments, the button may be a dome switch, rocker switch, electrical contact, magnetic switch, and so on. In some embodiments the button may be waterproof or otherwise sealed against the environment.

Various embodiments may include or otherwise incorporate one or more motion sensors. A motion sensor may detect motion of the device and provide, modify, cease, or otherwise affect a state, output, or input of the device or associated applications based at least in part on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some embodiments may use a GPS sensor to facilitate or enable location and/or navigation assistance.

As shown in FIG. 10, the device 900 may also include one or more acoustic elements, including a speaker and/or a microphone. The speaker may include drive electronics or circuitry and may be configured to produce an audible sound or acoustic signal in response to a command or input. Similarly, the microphone may also include drive electronics or circuitry and is configured to receive an audible sound or acoustic signal in response to a command or input. The speaker and the microphone may be acoustically coupled to port or opening in the case that allows acoustic energy to pass, but may prevent the ingress of liquid and other debris.

Certain embodiments may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

In certain embodiments, an electronic device may include one or more haptic modules for providing haptic feedback to the user. The embodiments described herein may relate to or take the form of one or more haptic actuators suitable to provide perceivable haptic feedback. Such actuators may include an electromagnetic coil, a permanent magnet or other magnetic field source. The magnetic field may induce motion in a mass of the haptic actuator by exerting a Lorentz force on the mass when the coil is energized. A direction of current through the coil determines the direction of motion of the mass, while the strength of the magnetic field determines the velocity of the mass and thus the magnitude of the haptic output.

In general, haptic actuators implemented in some embodiments may be configured to maximize or enhance resultant mechanical energy, given a very compact form factor of the electronic device.

In one embodiment, the haptic actuator may have a mass at least partially disposed within the coil when the mass is in a rest state. This mass may include two magnets of opposing polarities implemented as a magnet array affixed within a frame; the frame may provide extra weight to the mass and thus a stronger haptic output may be generated. A shaft may extend through the mass such that the mass may freely slide on the shaft.

The magnet array may generate a radial magnetic field that interacts with the magnetic field of the coil when the coil is energized by a current. The Lorentz force resulting from the interaction of the magnetic fields causes the mass to move along a shaft in a first direction. Reversing current flow through the coil reverses the Lorentz force. As a result, the magnetic field or force on the central magnet array is also reversed and the mass may move in a second direction. Thus, mass may move in both directions along the shaft, depending on the direction of current flow through the coil. Passing an alternating current through the coil may cause the central magnet array to move back and forth along a shaft.

In order to prevent the central magnet array from being attracted to the shaft, which could increase friction between the two and thereby increase the force necessary to move the central magnet array and frame, the shaft may be formed from a non-ferritic material such as tungsten, titanium, stainless steel, or the like.

The actuator also may have structures that provide restoring force to the mass. For example, a spring may be located at either end of the shaft. As the mass impacts the spring, the spring compresses and stores kinetic energy. This kinetic energy may be released to return the mass along the shaft, thereby sending it to or near its initial starting position. The kinetic energy in the spring(s) may cooperate with the coil to move the magnet in such a fashion.

Although a linear actuator has been described herein, it should be appreciated that other types of actuators may be used in different embodiments. For example, some embodiments may employ a rotary actuator, a piezoelectric actuator, or any other suitable linear or non-linear actuator. Likewise, certain embodiments may employ multiple actuators working in concert.

Illustrative methods and systems for providing dynamic messages are described above. Some or all of these systems and methods may, but need not, be implemented at least partially by architectures such as those shown at least in FIGS. 1-10 above. While many of the embodiments are described above with reference to alerts and/or notifications, it should be understood that any type of electronic content may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a network server, the network server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen or keypad), and at least one output device (e.g., a display device, printer or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable storage media for containing code, or portions of code, can include any appropriate media known or used in the art such as, but not limited to, volatile and non-volatile, removable and non-removable media implemented in any method or technology for storage of information such as computer-readable instructions, data structures, program modules or other data, including RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices or any other medium which can be used to store the desired information and which can be accessed by the a system device. Based at least in part on the disclosure and teachings provided herein, a person of ordinary skill in the art will appreciate other ways and/or methods to implement the various embodiments. However, computer-readable storage media does not include transitory media such as carrier waves or the like.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a," "an," and "the," and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based at least in part on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. Additionally, conjunctive language such as the phrase "at least one of X, Y, and Z," unless specifically stated otherwise, should also be understood to mean X, Y, Z, or any combination thereof, including "X, Y, and/or Z."

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method for presenting a plurality of messages on a wearable computing device, comprising:
    determining, by the wearable computing device, a time interval for presenting the plurality of messages;
    presenting, on a user interface of the wearable computing device, a first message after expiration of the time interval;
    scheduling, based at least in part on the time interval, a second message;
    identifying, by the wearable computing device, that a usage threshold has been reached;
    presenting, based at least in part on the usage threshold being reached, an update message corresponding to the usage threshold being reached on the user interface of the wearable computing device;
    canceling, by the wearable computing device, the second message; and
    presenting, on the user interface of the wearable computing device, a new message based at least in part on expiration of the time interval starting from presentation of the update message corresponding to the usage threshold being reached.

2. The computer-implemented method of claim 1, further comprising identifying, by the wearable computing device, a first use of the wearable computing device.

3. The computer-implemented method of claim 2, wherein the first message is presented after expiration of the time interval starting from the first use of the wearable computing device.

4. The computer-implemented method of claim 1, wherein at least one of the first message, the second message, the update message, or the new message are one of the plurality of messages.

5. The computer-implemented method of claim 1, wherein the second message is scheduled to be presented after expiration of the time interval starting from the first message.

6. The computer-implemented method of claim 1, wherein the usage threshold is associated with use of the wearable computing device.

7. The computer-implemented method of claim 1, wherein at least one of the first message or the second message are configured to provide information associated with the usage threshold.

8. A computer-readable storage medium storing computer-executable instructions for presenting a plurality of messages on a wearable computing device that, when executed by one or more processors of the wearable computing device, configure the one or more processors to at least:
    determine an amount of time for presenting the plurality of messages;
    present, on a user interface of the wearable computing device, a first message after the amount of time;
    schedule a second message based at least in part on the amount of time;
    identify that a usage threshold has been met; and
    based at least in part on the usage threshold being met:
        present an update message corresponding to the usage threshold being met on the user interface of the wearable computing device;
        cancel the second message; and
        present, on the user interface of the wearable computing device, a new message after the amount of time has passed from presentation of the update message.

9. The computer-readable storage medium of claim 8, wherein the amount of time is determined based at least in part on historical activity information associated with the wearable computing device.

10. The computer-readable storage medium of claim 8, wherein the one or more processors are further configured to at least identify a first use of the wearable computing device.

11. The computer-readable storage medium of claim 10, wherein the first message is presented after the amount of time has passed from the first use of the wearable computing device.

12. The computer-readable storage medium of claim 8, wherein the second message is scheduled to be presented after the amount of time has passed from the first message.

13. The computer-readable storage medium of claim 8, wherein the usage threshold is associated with use of the wearable computing device.

14. The computer-readable storage medium of claim 8, wherein at least one of the first message or the second message are configured to provide information associated with the usage threshold.

15. A wearable device configured to present a plurality of messages, comprising:
- a display device;
- a memory configured to store computer-executable instructions; and
- one or more processors in communication with the memory and the display device, the one or more processors configured to execute the computer-executable instructions to at least:
  - determine a time interval for presenting the plurality of messages;
  - present, on a user interface of the display device, a first message after expiration of the time interval;
  - schedule, based at least in part on the time interval, a second message;
  - identify that a usage threshold has been reached; and
  - based at least in part on the usage threshold being reached:
    - present an update message corresponding to the usage threshold being reached on the user interface of the display device;
    - cancel the second message; and
    - present, on the user interface of the display device, a new message based at least in part on expiration of the time interval starting from presentation of the update message.

16. The wearable device of claim 15, wherein the time interval is determined based at least in part on historical activity information associated with the wearable device.

17. The wearable device of claim 15, wherein the one or more processors are further configured to execute the computer-executable instructions to at least identify a first use of the wearable device.

18. The wearable device of claim 17, wherein the first message is presented after expiration of the time interval starting from the first use of the wearable computing device.

19. The wearable device of claim 15, wherein the second message is scheduled to be presented after expiration of the time interval starting from the first message.

20. The wearable device of claim 15, wherein at least one of the first message or the second message are configured to provide information associated with the usage threshold.

* * * * *